United States Patent [19]
Kato et al.

[11] Patent Number: 5,006,458
[45] Date of Patent: * Apr. 9, 1991

[54] ANALYTICAL ELEMENT HAVING A POLYACRYLAMIDE OR DERIVATIVE TO MINIMIZE BACKGROUND FOR ASSAYING ENZYME ACTIVITY

[75] Inventors: Keiko Kato; Shigeki Kageyama; Yoshikazu Amano; Fuminori Arai; Harumi Katsuyama, all of Saitama, Japan

[73] Assignee: Fuji Photo Film Co., Ltd., Kanagawa, Japan

[*] Notice: The portion of the term of this patent subsequent to Dec. 26, 2006 has been disclaimed.

[21] Appl. No.: 135,670

[22] Filed: Dec. 21, 1987

[30] Foreign Application Priority Data

Dec. 22, 1986 [JP] Japan .................................. 61-305886

[51] Int. Cl.$^5$ .......................... C12Q 1/00; C12Q 1/26
[52] U.S. Cl. ............................................ 435/4; 435/25; 435/26; 435/27; 435/28; 435/805; 436/810; 436/904; 422/55; 422/56; 422/57
[58] Field of Search ................................ 435/4, 25–28, 435/805; 436/810, 904; 422/55–57

[56] References Cited

U.S. PATENT DOCUMENTS

| 4,283,491 | 8/1981 | Dappen | 435/25 X |
|---|---|---|---|
| 4,557,901 | 12/1985 | Koyama et al. | 422/56 |
| 4,803,159 | 2/1989 | Smith-Lewis | 435/26 |
| 4,889,797 | 12/1989 | Amano et al. | 435/4 |

FOREIGN PATENT DOCUMENTS

| 0162302 | 11/1985 | European Pat. Off. . | |
| 0239990 | 10/1987 | European Pat. Off. . | |
| 0264079 | 4/1988 | European Pat. Off. . | |
| 3540526 | 5/1987 | Fed. Rep. of Germany | 422/57 |

Primary Examiner—Esther L. Kepplinger
Assistant Examiner—Carol A. Spiegel
Attorney, Agent, or Firm—Fisher, Nissen, Goldberg & Kiel McAulay

[57] ABSTRACT

A dry-type analytical element suitable for measuring enzyme activity of in a liquid sample, characterized by incorporating a polyacrylamide, polymethacrylamide or their derivatives into at least one water-permeable layer. The background concentration of the dry-type analytical element exhibits minimal increase even under a fluorescent light, and allows an accurate measured value to be easily obtained.

16 Claims, No Drawings

ANALYTICAL ELEMENT HAVING A POLYACRYLAMIDE OR DERIVATIVE TO MINIMIZE BACKGROUND FOR ASSAYING ENZYME ACTIVITY

BACKGROUND OF THE INVENTION

1. Field of the Invention

This invention relates to a dry-type analytical element suitable for measuring the enzyme activity of a liquid sample, particularly a biological body fluid.

2. Description of the Prior Art

A known dry-type analytical element for measuring lactate dehydrogenase (LDH) contains lactic acid or its salt and nicotinamide adenine dinucleotide coenzyme (NAD+) of the oxidized form in its water-permeable layer and nicotinamide adenine dinucleotide coenzyme of reduced form (NADH) is detected by a coloring reagent or the like. Such an analytical element for LDH activity assey is disclosed in Japanese patent KOKAI 59-88097, etc., and it is suitable for measuring the LDH activity of a liquid sample. In such analytical elements, the density of the background sometimes increases during the handling required for measurement, and as a result, the calibration curve previously prepared cannot be utilized. This phenomenon was remarkable, when polyvinylpyrrolidone known as the stabiliser and NAD+ (Japanese Patent KOKOKU 49-27717) was added to the water-permeable layer containing NAD+ as the binder.

SUMMARY OF THE INVENTION

The present inventors have investigated this problem, and have found that when the LDH activity analytical element containing NAD+ in a water-permeable layer is left for a long time under a light, particularly a fluorescent light the background density increases.

An object of the invention is to provide an analytical element suitable for measuring the LDH activity of a liquid sample having one or more water-permeable layers, at least one of the water-permeable layers being a porous spreading layer and at least one of the water-permeable layers containing lactic acid or its salt and NAD+, wherein increase of the background during handling is minimized, and thereby, an accurate measured value can easily be obtained.

Another object of the invention is to provide an analytical element suitable for measuring the enzyme activity of a liquid sample, which measurement is not limited to LDH activity of a liquid sample. The element has one or more water-permeable layers, with at least one of the water-permeable layers containing a substrate of the enzyme and NAD+. The element exhibits minimal increase of the background during handling, allowing an accurate measured value to be easily obtained.

Such objects have been achieved by incorporating a polymer and acrylamide, methacrylamide or their derivatives into a water-permeable layer of the analytical element.

Thus, the present invention provides a dry-type analytical element suitable for measuring the enzyme activity of a liquid sample. The element has one or more water-permeable layers wherein, at least one of the water-permeable layers is a porous spreading layer, and at least one of the water-permeable layers contains NAD+. In such an analytical element, the analytical element of the invention is characterized by that at least one of the water-permeable layers contains a hydrophilic polymer of acrylamide, methacrylamide or their derivatives.

DESCRIPTION OF THE PREFERRED EMBODIMENTS

The hydrophilic polymer usable in the analytical element of the invention is a polymer of the monomer component shown in the general formula [I] or a copolymer of this monomer component and other monomer component(s).

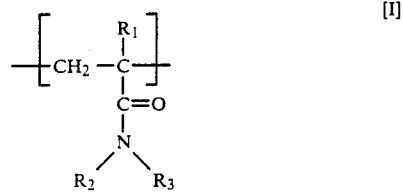

In the formula, $R_1$ represents a hydrogen atom or a lower alkyl group, and $R_2$ and $R_3$ represent a hydrogen atom, an aliphatic hydrocarbon group or an aromatic hydrocarbon group. $R_2$ may be identical with or different from $R_3$. $R_2$ may be joined to $R_3$ to form a ring, such as, piperidine or morpholine ring.

The lower alkyl group of $R_1$ includes the methyl group. Examples of $R_2$ and $R_3$ other than hydrogen atom include the methyl group, ethyl group, benzyl group, hydroxyethyl group, cyclohexyl group, phenyl group, piperidino group and morpholino group.

Examples of the monomer shown in the general formula [I] are acrylamide, N-methylacrylamide, N-ethylacrylamide, N-isopropylacrylamide, N,N-dimethylacrylamide, N-acryloylpiperidine, methacrylamide, N-methylmethacrylamide, N-ethylmethacrylamide, N-isopropylmethacrylamide and N,N-dimethylmethacrylamide.

The other monomer component in the case of the copolymer includes acrylic acid, methacrylic acid, maleic acid, methylacrylate, ethylmethacrylate, styrene and ethylene. In addition, the monomers and copolymerized components described in the specification of Japanese Patent Application No. 61-143754 are also usable. The copolymer may be composed of two or more kinds of the monomer component shown in the general formula [I]. The copolymer may be composed of more than two kinds of monomers.

The hydrophilic polymer employed in the invention is water-soluble, and its molecular weight is about 5,000 to 2,000,000, preferably 20,000 to 500,000.

The hydrophilic polymer is incorporated into a water-permeable layer of the analytical element, preferably the water-permeable layer containing NAD+. The hydrophilic polymer may be incorporated into the two or more water-permeable layers. The porous spreading layer is the most preferable layer to incorporate the hydrophilic polymer. The suitable content of the hydrophilic polymer is about 0.2 to 10 mg/m², preferably 0.5 to 5 mg/m².

The analytical element of the invention is suitable for measuring enzyme activity, and it comprises NAD+. Such an analytical element usually contains a substrate and reagents capable of reacting with NADH to generate a detectable change such as coloration, discoloration or emission of fluorescence. As such reagents, a combination of an electron carrier and a formazan dye precursor is preferable. The electron carrier may be selected from diaphorase, N-methylphenazonium methosulfate and the like. The most preferable formazan dye precursor is Nitrotetrazolium Blue (NTB or NBT, 3,3'-(3,3'-dimethoxy-4,4'-biphenylene)-bis [2-(p-nitrophenyl)-5-phenyltetrazolium chloride]). However, other formazan dye precursors such as INT (2-(p-iodophenyl)-3-(p-nitrophenyl)-5-phenltetrazolium chloride), BT (3,3'-(3,3'-dimethoxy-4,4'-biphenylene)-bis[2,5-diphenyltetrazolium chloride]), 3,3'-(4,4'-biphenylene)-bis [2,5-diphenyltetrazolium chloride] and the like are also usable. The substrate is selected according to the kind of the enzyme to be measured, and in the case of LDH, lactic acid or its salt is employed. Examples of other enzymes than LDH are aldehyde reductase, glycerol dehydrogenase, malate dehydrogenase and the like.

NAD+ and the substrate are incorporated into reagent layer, spreading layer or other water-permeable layer(s). They may be incorporated into the same layer, or they may separately be incorporated into different layers. Moreover, either of them may be incorporated into two or more layers, such as, the spreading layer and reagent layer, light-blocking layer and reagent layer, first reagent layer and second reagent layer, or spreading layer and first reagent layer. In such cases, the contents in the two or more layers may be different from each other. The porous spreading layer is the most preferable layer to incorporate NAD+ and the substrate. In any event, the substrate is also preferably incorporated into the layer containing the hydrophilic polymer. The contents of NAD+ and the substrate may be identical with a conventional analytical element. The reagents capable of reacting with NADH are also incorporated into the reagent layer, spreading layer or other water-permeable layer(s). They may be incorporated into the same layer or different layers, and either of them may be incorporated into one layer or two or more layers.

The present invention can be applied to various known dry-type analytical elements. The analytical element may be a multilayer element containing a support and water-permeable layer(s), such as, a registration layer, a light-blocking layer, a reagent layer, a porous spreading layer (hereinafter shortly referred to as spreading layer), an adhesive layer, a filtering layer, a water-absorption layer, an undercoating layer and other known layers. Some embodiments are disclosed in U.S. Pat. No. 3,992,158, U.S. Pat. No. 4,042,335 and Japanese Patent KOKAI 55-164356.

The following embodiments may be used in practice for the analytical elements of the invention containing a support.

(1) A spreading layer also utilized as a reagent layer superposed on the support. A water-absorption layer may be incorporated between the spreading layer and the support.

(2) A spreading layer, a reagent layer and the support superposed in this order. A water-absorption layer may be incorporated between the reagent layer and the support. The hydrophilic polymer is incorporated in either or both of the spreading layer and the reagent layer.

(3) A spreading layer, a reagent layer, a registration layer and the support superposed in this order. The hydrophilic polymer dye is incorporated in either or both of the spreading layer and the reagent layer.

(4) A spreading layer, a light-reflecting layer, a reagent layer and the support superposed in this order. One or more of the spreading layer, the light-reflecting layer and the reagent layer contain the hydrophilic polymer.

(5) A spreading layer also utilized as a reagent layer, a light-reflecting layer, a registration layer and the support superposed in this order. The spreading layer contains the hydrophilic polymer.

(6) A spreading layer, a light-reflecting layer, a reagent layer, a registration layer and the support superposed in this order. Either or both of the spreading layer and the reagent layer contains the hydrophilic polymer.

(7) A spreading layer, a reagent layer, a light-reflecting layer, a registration layer and the support superposed in this order. At least, the spreading layer or the reagent layer contains the hydrophilic polymer.

(8) A spreading layer, a first reagent layer, a light-reflecting layer, a second reagent layer, a registration layer and the support superposed in this order. At least, the second reagent layer or one of the layers located on the side contrary to the support therefrom contains the hydrophilic polymer.

Preferable embodiments for the present invention are (2) and (4). In any embodiment of (2) to (8), a water-absorption layer may be incorporated between the reagent layer or the registration layer and the support. In the embodiment of (2) or (3), a filtering layer may be incorporated between the reagent layer and the registration layer or the spreading layer or between plural reagent layers. In any embodiment of (4) to (8), a filtering layer may be incorporated between the light-reflecting layer and the spreading layer, the reagent layer or the registration layer, between the reagent layer and the registration layer, between the spreading layer and the reagent layer, or between the first reagent layer and the second reagent layer.

The water-impermeable light-transmissive support includes a transparent film or sheet made of polyethylene terephthalate, polycarbonate, polystyrene, cellulose ester such as cellulose triacetate and cellulose acetate propionate, or the like. The thickness of the support is usually in the range of about 50 $\mu$m to about 1 mm, preferably from about 80 $\mu$m to about 300 $\mu$m. The support may be provided with an undercoating layer on its surface in order to strengthen the adhesion of the layer laminated on it, such as, a registration layer. Instead of the undercoating layer, the surface of the support may be treated by a physical activation, such as, glow discharge or corona discharge or by a chemical activation.

The registration layer or the water-absorption layer provided on the support is preferably composed of a hydrophilic binder, that is, a hydrophilic polymer which absorbs water to swell. The registration layer is the layer where a color material produced from the indicator diffuses, and the water-absorption layer is the layer where the color material cannot substantially diffuse. The hydrophilic polymer is generally a natural or synthetic hydrophilic polymer having a swelling ratio in the range of about 1.5 to about 20 preferably from about 2.5 to about 15 at a water absorption at 30° C. Examples of the hydrophilic polymer are gelatins, such as, alkali-treated gelatin, acid-treated gelatin and deionized gelatin, gelatin derivatives, such as, phthalated gelatin, agarose and polyacrylamide. The thicknesses of the registration layer and water-absorption layer are usually in the range of about 1 $\mu$m to about 50 $\mu$m, preferably about 3 $\mu$m to 30 $\mu$m in the dry state. These layers may contain a surfactant, such as, a cationic surfactant, an anionic surfactant, an ampholytic surfactant or a nonionic surfactant and a pH buffer.

An adhesive layer may be provided for laminating a spreading layer on a water-absorption layer, registration layer, light-reflecting layer, filtering layer, reagent layer or the like. The adhesive layer is preferably composed of a hydrophilic polymer capable of adhering to the spreading layer when the adhesive layer is dampened or absorbs water to swell. Such a hydrophilic polymer may be selected from the hydrophilic polymers usable for the registration layer described above. Preferably hydrophilic polymers are gelatins, gelatin derivatives, polyacrylamide and the like. The thickness of the adhesive layer is usually in the range of about 0.5 $\mu$m to about 20 $\mu$m, preferably about 1 $\mu$m to about 10 $\mu$m in dry state. The adhesive layer may be provided for the adhesion of other layer. The adhesive layer is formed by applying an aqueous solution of a hydrophilic polymer and other compound added, if necessary.

The reagent layer of the analytical element of the invention may contain a hydrophilic polymer and a pH buffer, if necessary. Examples of the hydrophilic polymer include starch, cellulose, agarose, gelatin and their derivatives such as phthalated gelatin, polyacrylamide, copolymers of acrylamide and various vinyl monomer, polymethacrylamide and copolymers of methacrylamide and various vinyl monomers. The pH buffers suitable for the reagent layer include carbonate buffers, borate buffers, phosphate buffers and Good's buffers. Examples of these buffers are described in "Tanpakushitsu.Koso no Kiso-Jikken Ho (Fundamental Experimental Method of Proteins, Enzymes)" (Horio et al., Nankodo, Japan, 1981).

The light-reflecting layer blocks the color of the sample spotted on the spreading layer. In the case of a whole blood sample, this is due to hemoglobin. The light blocking effect takes place at the time of measuring the optically detectable change, such as, the color change or coloration occurring in the registration layer, reagent layer or other layer(s), from the side of the light-transmissive support by reflection photometry. This layer functions either as a light-blocking layer or a background layer. The light-reflecting layer is preferably a water-permeable layer composed of a hydrophilic polymer as binder wherein light-reflecting particles, such as, titanium dioxide or barium sulfate are dispersed. Examples of the hydrophilic polymer include the foregoing hydrophilic polymers usable for the registration layer, weakly hydrophilic regenerated cellulose and cellulose acetate. Preferable hydrophilic polymers are gelatins, gelatin derivatives and polyacrylamide. A known hardening agent may be added to the gelatin or a gelatin derivative. The light-reflecting layer may be formed by applying an aqueous solution of a hydrophilic polymer wherein titanium dioxide particles or the like are suspended followed by drying. In the analytical element of the invention, titanium dioxide particles or the like may be incorporated in spreading layer, reagent layer, registration layer or the like.

The spreading layer preferably has a metering action. The metering action is such that a sample spotted on the spreading layer spreads at a fixed amount per unit area without uneven distribution of any component in the sample in horizontal directions. The material constituting the matrix of the spreading layer may be filter paper, nonwoven fabric, woven fabrics, such as, plain weaves, knitted fabrics, such as, tricot fabric, glass fiber filter paper, membrane filter formed of blushed polymer, and three-dimensional lattice structure material composed of polymer particulates, etc. Preferable materials for the spreading layer are fibrous materials, such as, woven fabrics and knitted fabrics. These are explained in detail in U.S. Pat. No. 4,292,272, GB No. 2,087,074A and EP No. 0,162,302A. These woven fabrics and knitted fabrics are preferably degreased, such as, by washing.

The dry-type analytical element of the invention is preferably cut into square or circular pieces having a side or diameter of about 15 mm to about 30 mm, and put in a slide frame disclosed in Japanese Patent KOKAI 57-63452, U.S. Pat. No. 4,169,751, U.S. Pat. No. 4,387,990, PCT application WO No. 83/00391, etc. to use.

The measurement is carried out, for example, according to the manner disclosed in the specifications of the foregoing patents. An aqueous sample of about 5 $\mu$l to about 30 $\mu$l, preferably about 8 $\mu$l to about 15 $\mu$l is spotted on the spreading layer, and incubated at a definite temperature in the range of about 20° C. to about 45° C. for a prescribed time, if necessary. Thereafter, a color change or coloring in the analytical element is measured from the side of the support by reflection photometry, and the subject component in the sample is determined by the principle of colorimetry.

EXAMPLES

EXAMPLE 1

The support employed was a colorless transparent polyethylene terephthalate (PET) film having a thickness of 180 $\mu$m on which a gelatin undercoating was provided. The following aqueous solution was applied on the support at the rate of 133 cc/m² and then dried to form a dye-forming layer having a dry thickness of 10 $\mu$m.

| | |
|---|---|
| Gelatin | 190 g |
| Octylphenoxypolyethoxyethanol | 30 g |
| Nitrotetrazolium Blue* | 9.5 g |
| Water | 1,350 g |
| Adjusted to pH 6.5 by dil. NaOH solution. | |

*3,3'-(3,3'-dimethoxy 4,4'-biphenylene)-bis[2-(p-nitrophenyl)-5-phenyltetrazolium chloride]

The above dye-forming layer was moistened with 30 g/m² of water. A PET tricot fabric cloth knitted from 50 deniers PET spun yarn by 36 gauges was lightly pressed on it to laminate it as the spreading layer, followed by drying.

Subsequently, the following aqueous solution was uniformly applied on the spreading layer at the rate of 120 cc/m², and dried to obtain an integral multilayer analytical element for measuring LDH activity.

| | |
|---|---|
| Nonylphenoxypolyethoxyethanol (n = 40) | 1 g |
| Octylphenoxypolyethoxyethanol (n = 10) | 1 g |
| Tris(hydroxymethyl)aminomethane | 6 g |
| Lithium lactate | 3 g |
| Polyacrylamide | 25 g |
| (Molecular Weight; about 200,000) | |
| $\beta$-NAD+ | 0.6 g |
| Diaphorase | 150,000 U |
| Water | 100 g |
| Adjusted to pH 8.5 by dil. HCl solution. | |

A comparative analytical element 1 was prepared in the same manner as the above example except that 25 g of polyvinylpyrrolidone was added instead of 25 g of polyacrylamide.

These analytical elements were irradiated at 25° C. by a white fluorescent light ("NATIONAL FLUORESCENT LIGHT FLR/40S-W/M-X") at an illuminance of 1,000 luxes for the times described in Table 1. After the irradiation, reflection optical density of each element was measured at 540 nm from the side of the support. The results are tabulated in Table 1.

TABLE 1

| Irradiation | Reflection Optical Density | |
|---|---|---|
| Time (min.) | Invention | Comparative |
| 0 | 0.426 | 0.442 |
| 5 | 0.431 | 0.452 |
| 10 | 0.437 | 0.461 |
| 15 | 0.442 | 0.472 |
| 30 | 0.455 | 0.494 |
| Difference between 30 min. and 0 min. | 0.029 | 0.052 |

As shown in Table 1, the analytical element of the invention exhibits much less influence by a fluorescent light as compared to the comparative analytical element 1.

We claim:

1. In an analytical element for measuring enzyme activity of a liquid sample which has one or more water-permeable layers, and wherein at least one of the water-permeable layers is a porous spreading layer, the improvement which comprises said porous layer containing NAD+ and at least one of the water-permeable layers containing a water-soluble hydrophilic polymer having a molecular weight from about 5,000 to 500,000 selected from the group consisting of homopolymers formed from a monomer component having the formula I and copolymers of this monomer component and another monomer component(s):

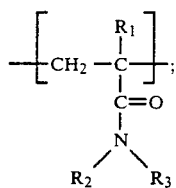

wherein $R_1$ represents a hydrogen atom or lower alkyl group, $R_2$ and $R_3$ represent a hydrogen atom, aliphatic hydrocarbon group, or aromatic hydrocarbon group, and $R_2$ may be identical with or different from $R_3$ and $R_2$ may be joined to $R_3$ to form a ring.

2. The analytical element of claim 1 wherein a second water-permeable layer contains NAD+ and lactic acid or its salt.

3. The analytical element of claim 2 wherein said second water-permeable layer further contains said hydrophilic polymer.

4. The analytical element of claim 1 wherein said porous spreading layer contains said hydrophilic polymer.

5. The analytical element of claim 4 wherein said porous spreading layer further contains lactic acid or its salt.

6. The analytical element of claim 1 wherein a second water-permeable layer contains NAD+ and an electron carrier and wherein said second water-permeable layer or at least a third water-permeable layer contains an electron acceptor dye precursor.

7. The analytical element of claim 6 wherein said second water-permeable layer containing NAD+ and an electron carrier further contains lactic acid or its salt.

8. The analytical element of claim 1 wherein said porous spreading layer further contains an electron carrier and lactic acid or its salt.

9. The analytical element of claim 8 wherein said porous spreading layer or a second water-permeable layer different from said porous spreading layer contains said electron acceptor dye precursor.

10. The element of claim 1 wherein $R_2$ and $R_3$ form a piperidine or morpholine ring.

11. The element of claim 1 wherein $R_1$ is methyl.

12. The element of claim 1 wherein $R_2$ and $R_3$ are selected from the group consisting of methyl, ethyl, benzyl, hydroxyethyl, cyclohexyl, and phenyl.

13. The element of claim 1 wherein the monomer component of formula I is selected from the group consisting of acrylamide, N-methylacrylamide, N-ethylacrylamide, N-isopropylacrylamide, N,N-dimethylacrylamide, N-acryloylpiperidine, methacrylamide, N-ethylmethacrylamide, N-isopropylmethacrylamide and N,N-dimethylmethacrylamide.

14. The analytical element of claim 1 wherein a hydrophilic copolymer is used and said other monomer is selected from the group consisting of acrylic acid, methacrylic acid, maleic acid, methylacrylate, ethylmethacrylate, styrene and ethylene.

15. The element of claim 1 wherein the polymer has a molecular weight from about 20,000 to 2,000,000.

16. The element of claim 1 wherein the amount of polymer is from about 0.2 to 10 mg/m$^2$.

* * * * *